(12) United States Patent
Gonzalez-Hernandez

(10) Patent No.: US 8,764,808 B2
(45) Date of Patent: Jul. 1, 2014

(54) BONE FIXATION SYSTEM

(76) Inventor: Eduardo Gonzalez-Hernandez, Coconut Grove, FL (US)

( * ) Notice: Subject to any disclaimer, the term of this patent is extended or adjusted under 35 U.S.C. 154(b) by 0 days.

(21) Appl. No.: 13/439,725

(22) Filed: Apr. 4, 2012

(65) Prior Publication Data

US 2012/0197308 A1 Aug. 2, 2012

Related U.S. Application Data

(63) Continuation of application No. 12/398,882, filed on Mar. 5, 2009.

(60) Provisional application No. 61/035,138, filed on Mar. 10, 2008.

(51) Int. Cl.
*A61B 17/80* (2006.01)

(52) U.S. Cl.
USPC .......................................... 606/280; 606/282

(58) Field of Classification Search
USPC ............................. 606/305, 70, 280, 71, 286
See application file for complete search history.

(56) References Cited

U.S. PATENT DOCUMENTS

| | | |
|---|---|---|
| 1,950,799 A | 3/1934 | Jones |
| 2,500,370 A | 3/1950 | McKibbin |
| 2,555,291 A | 5/1951 | Poupitch |
| 2,875,663 A | 3/1959 | Wieber |
| 3,489,143 A | 1/1970 | Halloran |
| 3,552,389 A | 1/1971 | Allgower et al. |
| 3,579,831 A | 5/1971 | Stevens et al. |
| 3,716,050 A | 2/1973 | Johnston |
| 3,791,380 A | 2/1974 | Dawidowski |
| 3,900,025 A | 8/1975 | Barnes, Jr. |
| 4,263,904 A | 4/1981 | Judet |
| 4,535,768 A | 8/1985 | Hourahane et al. |
| 4,683,878 A | 8/1987 | Carter |
| 4,733,654 A | 3/1988 | Marino |
| 4,776,330 A | 10/1988 | Chapman et al. |
| 4,790,302 A | 12/1988 | Colwill et al. |
| 4,794,919 A | 1/1989 | Nilsson |
| 4,838,264 A | 6/1989 | Bremer et al. |
| 4,858,602 A | 8/1989 | Seidel et al. |
| 4,870,957 A | 10/1989 | Goble et al. |
| 5,003,969 A | 4/1991 | Azer et al. |

(Continued)

FOREIGN PATENT DOCUMENTS

| DE | 86 28 766 U1 | 12/1986 |
|---|---|---|
| DE | 89 07 443 U1 | 9/1989 |

(Continued)

OTHER PUBLICATIONS

Postak, Paul D.; "Biomechanical Properties of Fixed-Angle Velar Distal Radius Plates Under Dynamic Loading;" 2007; 6 pages.

(Continued)

*Primary Examiner* — Matthew Lawson
*Assistant Examiner* — Zade Coley
(74) *Attorney, Agent, or Firm* — Martin & Ferraro, LLP

(57) ABSTRACT

The invention provides embodiments of a bone fixation system having a bone plate and a specialized screws system. The bone plate includes one or more bi-directional combination holes that can accommodate two bone screws in the same hole, the screws being oriented in non-parallel direction. In accommodating two screws in the same hole, one of the screws has a by-pass head.

29 Claims, 8 Drawing Sheets

(56) References Cited

U.S. PATENT DOCUMENTS

| | | | |
|---|---|---|---|
| 5,015,248 A | 5/1991 | Burstein et al. | |
| 5,041,113 A * | 8/1991 | Biedermann et al. | 606/288 |
| 5,041,114 A | 8/1991 | Chapman et al. | |
| 5,180,383 A | 1/1993 | Haydon | |
| 5,190,544 A | 3/1993 | Chapman et al. | |
| 5,324,291 A | 6/1994 | Ries et al. | |
| 5,356,410 A | 10/1994 | Pennig | |
| 5,364,399 A * | 11/1994 | Lowery et al. | 606/295 |
| 5,423,860 A | 6/1995 | Lizardi et al. | |
| 5,437,667 A | 8/1995 | Papierski et al. | |
| 5,443,516 A | 8/1995 | Albrektsson et al. | |
| 5,458,654 A | 10/1995 | Tepic | |
| 5,462,547 A | 10/1995 | Weigum | |
| 5,472,444 A | 12/1995 | Huebner et al. | |
| 5,505,734 A | 4/1996 | Caniggia et al. | |
| 5,578,035 A | 11/1996 | Lin | |
| 5,584,835 A | 12/1996 | Greenfield | |
| 5,586,985 A | 12/1996 | Putnam et al. | |
| 5,601,553 A | 2/1997 | Trebing et al. | |
| 5,620,449 A | 4/1997 | Faccioli et al. | |
| 5,658,287 A | 8/1997 | Hofmann et al. | |
| 5,665,088 A | 9/1997 | Gil et al. | |
| 5,674,222 A | 10/1997 | Berger et al. | |
| 5,676,667 A | 10/1997 | Hausman | |
| 5,681,311 A * | 10/1997 | Foley et al. | 606/283 |
| 5,709,686 A | 1/1998 | Talos et al. | |
| 5,749,872 A | 5/1998 | Kyle et al. | |
| 5,766,174 A | 6/1998 | Perry | |
| 5,776,194 A | 7/1998 | Mikol et al. | |
| 5,779,704 A | 7/1998 | Kim | |
| 5,785,712 A | 7/1998 | Runciman et al. | |
| 5,840,078 A | 11/1998 | Yerys | |
| 5,868,749 A | 2/1999 | Reed | |
| 5,931,839 A | 8/1999 | Medoff | |
| 5,976,139 A | 11/1999 | Bramlet | |
| 6,030,389 A | 2/2000 | Wagner et al. | |
| 6,096,040 A | 8/2000 | Esser | |
| 6,149,653 A | 11/2000 | Deslauriers | |
| 6,152,927 A * | 11/2000 | Farris et al. | 606/287 |
| 6,200,330 B1 | 3/2001 | Benderev et al. | |
| 6,206,881 B1 | 3/2001 | Frigg et al. | |
| D443,060 S | 5/2001 | Benirschke et al. | |
| 6,270,499 B1 | 8/2001 | Leu et al. | |
| D449,692 S * | 10/2001 | Michelson | D24/155 |
| 6,302,887 B1 | 10/2001 | Spranza et al. | |
| 6,331,179 B1 | 12/2001 | Freid et al. | |
| 6,348,052 B1 | 2/2002 | Sammarco | |
| 6,358,250 B1 | 3/2002 | Orbay | |
| 6,364,881 B1 * | 4/2002 | Apgar et al. | 606/284 |
| 6,364,882 B1 | 4/2002 | Orbay | |
| 6,379,359 B1 | 4/2002 | Dahners | |
| 6,398,783 B1 * | 6/2002 | Michelson | 606/70 |
| 6,406,478 B1 | 6/2002 | Kuo | |
| 6,409,768 B1 | 6/2002 | Tepic et al. | |
| 6,413,259 B1 | 7/2002 | Lyons et al. | |
| 6,440,135 B2 | 8/2002 | Orbay et al. | |
| 6,468,278 B1 | 10/2002 | Muckter | |
| 6,572,620 B1 | 6/2003 | Schon et al. | |
| 6,620,195 B2 | 9/2003 | Goble et al. | |
| 6,623,486 B1 | 9/2003 | Weaver et al. | |
| 6,663,669 B1 | 12/2003 | Reiley | |
| 6,669,701 B2 | 12/2003 | Steiner et al. | |
| 6,695,844 B2 | 2/2004 | Bramlet et al. | |
| 6,706,046 B2 | 3/2004 | Orbay et al. | |
| 6,712,820 B2 | 3/2004 | Orbay | |
| 6,719,759 B2 | 4/2004 | Wagner et al. | |
| 6,730,090 B2 | 5/2004 | Orbay et al. | |
| 6,776,781 B1 * | 8/2004 | Uwaydah | 606/279 |
| 6,863,671 B1 * | 3/2005 | Strobel et al. | 606/314 |
| 6,866,665 B2 | 3/2005 | Orbay | |
| 6,916,323 B2 | 7/2005 | Kitchens | |
| 6,945,973 B2 | 9/2005 | Bray | |
| 7,001,388 B2 | 2/2006 | Orbay et al. | |
| 7,063,701 B2 | 6/2006 | Michelson | |
| 7,128,744 B2 | 10/2006 | Weaver et al. | |
| D536,453 S | 2/2007 | Young et al. | |
| 7,220,246 B2 | 5/2007 | Raulerson | |
| 7,229,445 B2 * | 6/2007 | Hayeck et al. | 606/70 |
| 7,235,079 B2 | 6/2007 | Jensen et al. | |
| 7,354,441 B2 | 4/2008 | Frigg | |
| 7,500,983 B1 | 3/2009 | Kaiser et al. | |
| 7,563,263 B2 | 7/2009 | Orbay et al. | |
| 7,582,107 B2 | 9/2009 | Trail et al. | |
| 7,591,823 B2 | 9/2009 | Tipirneni | |
| 7,604,657 B2 | 10/2009 | Orbay et al. | |
| 7,637,908 B1 | 12/2009 | Gonzalez-Hernandez | |
| 7,651,517 B2 | 1/2010 | Konieczynski et al. | |
| 7,655,029 B2 | 2/2010 | Niederberger et al. | |
| 7,695,472 B2 | 4/2010 | Young | |
| 7,722,653 B2 | 5/2010 | Young et al. | |
| 7,740,648 B2 | 6/2010 | Young et al. | |
| 7,744,638 B2 | 6/2010 | Orbay | |
| 7,776,076 B2 | 8/2010 | Grady, Jr. et al. | |
| 7,780,667 B2 | 8/2010 | Watanabe et al. | |
| 7,780,710 B2 | 8/2010 | Orbay et al. | |
| 7,896,886 B2 | 3/2011 | Orbay et al. | |
| 7,909,859 B2 | 3/2011 | Mosca et al. | |
| 7,914,532 B2 | 3/2011 | Shaver et al. | |
| 7,927,341 B2 | 4/2011 | Orbay et al. | |
| 7,938,850 B2 | 5/2011 | Orbay et al. | |
| 7,951,176 B2 | 5/2011 | Grady et al. | |
| 7,951,178 B2 | 5/2011 | Jensen | |
| D643,121 S | 8/2011 | Milford et al. | |
| D646,785 S | 10/2011 | Milford | |
| 8,062,367 B2 * | 11/2011 | Kirschman | 623/17.11 |
| 8,100,953 B2 | 1/2012 | White et al. | |
| 8,182,485 B1 | 5/2012 | Gonzalez-Hernandez | |
| 8,574,234 B2 | 11/2013 | Gonzalez-Hernandez | |
| 2003/0135212 A1 | 7/2003 | Chow | |
| 2003/0135216 A1 | 7/2003 | Sevrain | |
| 2004/0097939 A1 | 5/2004 | Bonutti | |
| 2004/0193278 A1 | 9/2004 | Maroney et al. | |
| 2004/0210220 A1 | 10/2004 | Tornier | |
| 2005/0004574 A1 | 1/2005 | Muckter | |
| 2005/0015089 A1 * | 1/2005 | Young et al. | 606/69 |
| 2005/0021033 A1 | 1/2005 | Zeiler et al. | |
| 2005/0038513 A1 * | 2/2005 | Michelson | 623/17.11 |
| 2005/0085819 A1 | 4/2005 | Ellis et al. | |
| 2005/0240187 A1 | 10/2005 | Huebner et al. | |
| 2005/0261688 A1 * | 11/2005 | Grady et al. | 606/69 |
| 2005/0267476 A1 | 12/2005 | Chervitz et al. | |
| 2005/0288681 A1 | 12/2005 | Klotz et al. | |
| 2006/0015072 A1 | 1/2006 | Raulerson | |
| 2006/0015101 A1 | 1/2006 | Warburton et al. | |
| 2006/0161156 A1 | 7/2006 | Orbay | |
| 2006/0217722 A1 | 9/2006 | Dutoit et al. | |
| 2006/0235400 A1 * | 10/2006 | Schneider | 606/69 |
| 2006/0241617 A1 | 10/2006 | Holloway et al. | |
| 2006/0264946 A1 * | 11/2006 | Young | 606/69 |
| 2006/0264947 A1 | 11/2006 | Orbay et al. | |
| 2006/0264956 A1 | 11/2006 | Orbay et al. | |
| 2007/0005074 A1 | 1/2007 | Chudik | |
| 2007/0016205 A1 | 1/2007 | Buetter et al. | |
| 2007/0083207 A1 * | 4/2007 | Ziolo et al. | 606/73 |
| 2007/0123880 A1 | 5/2007 | Medoff | |
| 2007/0123885 A1 | 5/2007 | Kirschman | |
| 2007/0162015 A1 | 7/2007 | Winquist et al. | |
| 2007/0167953 A1 | 7/2007 | Prien et al. | |
| 2007/0233114 A1 | 10/2007 | Bouman | |
| 2007/0233115 A1 | 10/2007 | Sixto et al. | |
| 2008/0015593 A1 | 1/2008 | Pfefferle et al. | |
| 2008/0045960 A1 | 2/2008 | Bruecker et al. | |
| 2008/0132955 A1 | 6/2008 | Frigg | |
| 2008/0140130 A1 | 6/2008 | Chan et al. | |
| 2008/0154311 A1 | 6/2008 | Staeubli | |
| 2008/0161853 A1 | 7/2008 | Arnold et al. | |
| 2008/0161860 A1 | 7/2008 | Ahrens et al. | |
| 2008/0161863 A1 | 7/2008 | Arnold et al. | |
| 2008/0221577 A1 | 9/2008 | Elghazaly | |
| 2008/0234749 A1 | 9/2008 | Forstein | |
| 2008/0234752 A1 | 9/2008 | Dahners | |
| 2008/0249572 A1 | 10/2008 | Tandon | |
| 2009/0012571 A1 | 1/2009 | Perrow et al. | |
| 2009/0024173 A1 | 1/2009 | Reis, Jr. | |

(56) References Cited

U.S. PATENT DOCUMENTS

| | | |
|---|---|---|
| 2009/0048681 A1 | 2/2009 | Vlachos |
| 2009/0076554 A1 | 3/2009 | Huebner et al. |
| 2009/0105838 A1 | 4/2009 | Russo et al. |
| 2009/0171399 A1* | 7/2009 | White et al. ............. 606/286 |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0264936 A1 | 10/2009 | Gonzalez-Hernandez |
| 2009/0275987 A1 | 11/2009 | Graham et al. |
| 2009/0275991 A1 | 11/2009 | Medoff |
| 2009/0281578 A1 | 11/2009 | Spencer |
| 2009/0299369 A1 | 12/2009 | Orbay et al. |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0030276 A1 | 2/2010 | Huebner et al. |
| 2010/0057086 A1 | 3/2010 | Price et al. |
| 2010/0145339 A1 | 6/2010 | Steffen |
| 2010/0217393 A1 | 8/2010 | Theofilos |
| 2010/0262194 A1 | 10/2010 | Wagner et al. |
| 2010/0274245 A1 | 10/2010 | Gonzalez-Hernandez |
| 2010/0324602 A1 | 12/2010 | Huebner et al. |
| 2010/0331844 A1 | 12/2010 | Ellis et al. |
| 2011/0152943 A1 | 6/2011 | Gonzalez-Hernandez |
| 2012/0083848 A1 | 4/2012 | Gonzalez-Hernandez |
| 2012/0109322 A1 | 5/2012 | Gonzalez-Hernandez |
| 2012/0197305 A1 | 8/2012 | Gonzalez-Hernandez |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |
| 2013/0116734 A1 | 5/2013 | Gonzalez-Hernandez |
| 2013/0289627 A1 | 10/2013 | Gonzalez-Hernandez |

FOREIGN PATENT DOCUMENTS

| | | | |
|---|---|---|---|
| DE | 43 43 117 A1 | 6/1995 | |
| DE | 198 57 279 A1 | 6/2000 | |
| DE | 299 07 161 U1 | 8/2000 | |
| EP | 0 551 588 A1 | 11/1992 | |
| EP | 1 132 052 A2 | 9/2001 | |
| EP | 1 468 655 A2 | 10/2004 | |
| FR | 2 606 268 A1 | 5/1988 | |
| FR | 2 680 673 A1 | 3/1993 | |
| JP | 4-138152 A | 5/1992 | |
| WO | WO 99/38448 A1 | 8/1999 | |
| WO | WO 2005/037117 | 4/2005 | |
| WO | WO 2008/007194 A2 | 1/2008 | |
| WO | WO 2008007196 A2 * | 1/2008 | ............. A61B 17/80 |

OTHER PUBLICATIONS

Synthes, "Large Fragment LCP Instrument and Implant Set;" technique guide; 2003; 31 pages.

Synthes, "Locking Compression Plate (LCP) System. Locking screw technology and conventional plating in one system;" 2003; 6 pages.

Synthes; Modular Mini Fragment LCP System (brochure); 2007; 12 pages.

Synthes; Small Fragment Locking Compression Plate (LCP) System (brochure); 2002; 43 pages.

Zimmer, Inc. "Zimmer® Universal Locking System," brochure (2006), 4 pages.

U.S. Appl. No. 10/993,723, filed Nov. 2004, Gonzalez-Hernandez.

U.S. Appl. No. 11/050,304, filed Feb. 2005, Gonzalez-Hernandez.

U.S. Appl. No. 11/079,350, filed Mar. 2005, Gonzalez-Hernandez.

U.S. Appl. No. 11/366,676, filed Mar. 2006, Gonzalez-Hernandez.

U.S. Appl. No. 11/493,122, filed Jul. 2006, Gonzalez-Hernandez.

U.S. Appl. No. 11/526,331, filed Sep. 2006, Gonzalez-Hernandez.

U.S. Appl. No. 11/707,775, filed Feb. 2007, Gonzalez-Hernandez.

U.S. Appl. No. 13/253,564, filed Oct. 2011, Gonzalez Hernandez.

U.S. Appl. No. 13/282,810, filed Oct. 2011, Gonzalez-Hernandez.

U.S. Appl. No. 13/411,069, filed Mar. 2012, Gonzalez-Hernandez.

U.S. Appl. No. 13/411,100, filed Mar. 2012, Gonzalez-Hernandez.

U.S. Appl. No. 13/412,039, filed Mar. 2012, Gonzalez-Hernandez.

Acumed; The Mayo Clinic Congruent Elbow Plates (catalog); 2003; 19 pages.

Acumed; The Mayo Clinic Congruent Elbow Plate System (catalog); Apr., 2006; 20 pages.

Christie, J., C.R. Howie and P.C. Armour, *Fixation of displaced subcapital femoral fractures. Compression screw fixation versus double divergent pins. J Bone Joint Surg [B]*1988; 70-B: 199-201.

Cross, W.M. e.t al., "Achieving stable fixation: biomechanical designs for fracture healing, " AAOS Now (2008) 4 pages.

Guha, AR, et al.; "A New Technique of Fixation of Radial Head Fractures Using a Modified Tubular Plate, " Journal of Postgraduate Medicine; July 2004; vol. 50, Issue 2; pp. 113-114; Accessed Aug. 6, 2008 at: http://wwvv.jpgmonline.com/articie.asp?issn,=0022-3859;year=2004;volume=50;issue=2;spage=113;epage=114;aulast=Guha.

Hand Innovations, LLC; DVR Anatomic, Volar Plating System; 2007; 4 pages.

Lakatos, R. et al.; "General principles of internal fixation"; eMedicine; Aug. 2006; 51 pages.

"MIS Technique," published by Zimmer®, 1 page (undated).

Robert, III, K.Q., R. Chandler, R,V, Barratta, K.A. Thomas and M.B. Harris, *The effect of divergent screw placement on the initial strength of plate-to-bone fixation. J Trauma.* Dec. 2003;55(6).1139-44.

Synthes; Locking Compression Plate (LCP) System (brochure); 2003: 6 pages.

Synthes: Locking Compression Plate (LCP) System (brochure); Jan. 2007; 6 pages.

Written Opinion of the International Searching Authority; International Application No. PCT/US2009/036211; Sep. 23, 2010; 8 pages.

"Zimmer® Universal Locking System," The Journal of Bone and Joint Surgery, vol. 89, No. 7, Jul. 2007, 1 page.

Zimmer, Inc.; "Zimmer Universal Locking System;" brochure; 2009, 2 pages.

Zimmer, Inc. "Zimmer Holdings to Launch Innovative Locking Plate System at Orthopaedic Trauma Association Meeting," Sep. 14, 2006; 3 pages.

Zimmer; Zimmer Periarticular Plating System-Low-Profile Fixation (catalog); 2003; 8 pages.

U.S. Appl. No. 13/663,129, filed Oct. 2012, Gonzalez-Hernandez.

U.S. Appl. No. 13/663,209, filed Oct. 2012, Gonzalez-Hernandez.

U.S. Appl. No. 13/840,194, filed Mar. 2013, Gonzalez-Hernandez.

\* cited by examiner

BONE FIXATION SYSTEM

The present application is a continuation of U.S. application Ser. No. 12/398,882, filed Mar. 5, 2009; which claims the benefit of U.S. Provisional Application No. 61/035,138, filed on Mar. 10, 2008; all of which are incorporated by reference herein.

BACKGROUND OF THE INVENTION

1. Field of the Invention

The present invention relates to a system and method for bone fracture fixation.

2. Description of the Prior Art

Conventional bone fracture fixation plate and screw systems work by drawing the fracture fragments to the plate, and if designed with "compression" holes, the fracture fragments can be made to compress against each other to promote primary bone healing. However, the angular relationship between the plate and screws is not fixed and can change postoperatively. As such, this can lead to misalignment and poor clinical results.

One method of securing the screw to a bone plate involves the use of so-called "locking screws." A locking screw has a male thread on an outer surface of its head that interfaces with a female thread on the plate to lock the screw to the plate. Bone plates having threaded holes for accommodating locking screws are known. For example, German Patent Application No. 43 43 117 discloses a bone plate with threaded holes for locking screws. As the relationship between the locking screws and the plate is fixed, locking screws provide a high resistance to shear or torsion forces. However, locking screws have a limited capability to compress bone fragments.

Another approach to construction of a bone plate involves use of "combination holes." Combination holes in the bone plates have a domain for non-locking screws and another domain for locking screws. The locking screws can only be applied in a direction perpendicular to the plate. (See, e.g., U.S. Pat. Nos. 6,669,701 and 7,354,441 to Frigg) However, only a one locking or a non-locking screw can be applied in each of these "combination" holes along the bone plates.

Another bone plate hole configuration involves a "figure-eight" hole. (See, e.g., Universal Locking System available from Zimmer Holdings, Inc. (Warsaw, Ind.); see, also J. Bone and Joint Surgery, 89(7) 2007.) The figure-eight hole in the a bone plate has two parallel threaded domains. A locking screw can be mated to one domain of the holes or to the other domain of the same hole. In either case, the locking screw can be applied only perpendicular to the bone plate. Further, only one screw can be applied in each of these "figure-eight" holes along the plate.

In yet another approach, the bone plate has individual locking holes for mating individual locking screws. (See, e.g., MIS Technique available from Zimmer Holdings, Inc. (Warsaw, Ind.)) The individual holes are oriented alternating in one direction and in another direction (in the plane transverse to the longitudinal axis of the plate) away from the perpendicular to the plate. However, for such a configuration, half of the screw holes may not be suitable for use. In the worse case scenario, none of the holes can be used.

SUMMARY OF THE INVENTION

A system and method for bone fracture fixation, especially long bone fracture fixation, in acute injury or reconstruction setting is provided. The system includes a bone plate and a specialized screw system. The bone plate has an upper surface and an opposed lower surface, which contacts the bone to be fixated. The bone plate includes at least one, and suitably a plurality of bi-directional divergent combination holes, spaced apart along its length. Each bi-directional combination hole has two screw domains. The central axis of the domains are at angles to each other and in reference to the lower plate surface, i.e., the directions of the screws positioned in each domain of a combination hole are non-parallel. The specialized screw system includes a by-pass head screw having a cut away such that "by-pass" head of the screw allows placement of a "full head" screw immediately adjacent in the same combination hole. The screws may have a threaded portion along their shafts or may be non-threaded pegs. The specialized screws may be locking (i.e., threaded head) or non-locking.

In some embodiments, the invention provides a bone plate which has a suitably serpentine shape to optimize the use of materials around the bi-directional holes. The bi-directional holes may be disposed adjacent but offset or angled to one another, e.g., along the length of a bone plate. In other embodiments, the invention provides a bone plate, which has a suitably linear shape. The combination holes may also be placed adjacent to one another but are offset or angled with respect to each other and with respect to the longitudinal axis of the plate. The central axis of the domains of the combination holes are configured at an angle with respect to each other and with respect to the lower plate surface. The bone plate may include both combination and non-combination holes.

In another aspect, a method of fixating bone fractures is provided which includes positioning a bone plate having a plurality of bi-directional divergent holes therethrough to a fracture site, and inserting bone screws through the bi-directional holes of the bone plate into a bone or bone fragments to fixate the fracture, the screws being oriented in the bone in non-parallel directions. A by-pass head screw allows accommodation of a full head screw in the same hole.

Other advantages and a better appreciation of the specific adaptations, variations, and physical attributes of the invention will be gained upon an examination of the following detailed description of the invention, taken in conjunction with the accompanying drawings.

DETAILED DESCRIPTION OF THE PREFERRED EMBODIMENT

Figure 1:
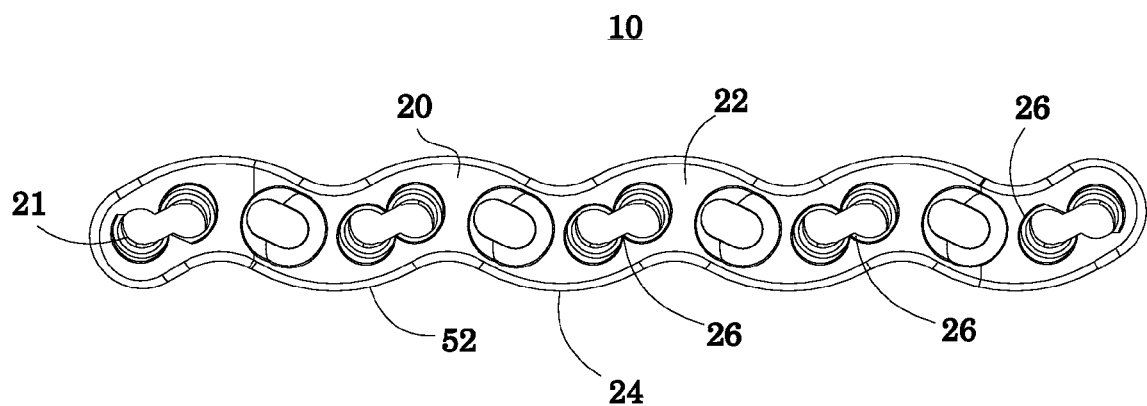
FIG. 1 is a top plan view of a serpentine plate configuration of a bone plate with a plurality of bi-directional screw holes, all in accordance with embodiments of the invention.

A bone fixation system embodying the principles illustrated in embodiments of the invention is provided. The system includes a bone plate and a specialized screw system.

Before any embodiments of the invention are explained in detail, it is to be understood that the invention is not limited in its application to the details of the structure and function set forth in the following description or illustrated in the appended drawings. The invention is capable of other embodiments and of being practiced or of being carried out in various ways.

Also, it is to be understood that the phraseology and terminology used herein is for the purpose of description and should not be regarded as limiting. The use of "comprising," "including," or "having" and variations thereof herein is meant to encompass the items listed thereafter and equivalents thereof as well as additional items. "Comprising" also encompasses the terms "consisting of" and "consisting essentially of." The use of "consisting essentially of" means, e.g., that a device may include additional features, but only if the additional features do not materially alter the basic and novel characteristics of the device.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Further, no admission is made that any reference, including any patent or patent document, citied in this specification constitutes prior art. In particular, it will be understood that unless otherwise stated, reference to any document herein does not constitute an admission that any of these documents forms part of the common general knowledge in the art in the United States or in any other country. Any discussion of the references states what their authors assert, and applicant reserves the right to challenge the accuracy and pertinence of any of the documents cited herein.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

Unless otherwise noted, technical terms are used according to conventional usage. However, as used herein, the following definitions may be useful in aiding the skilled practitioner in understanding the invention. Such definitions shall be applied, unless a different definition is given in the claims or elsewhere in this specification.

The term "bone screw", as used herein, refers to a screw configured to be inserted into bone. The screw may be threaded, or have a threaded portion, along its shaft, or may be non-threaded shaft, e.g., a non-threaded or smooth peg. The bone screw may also be a locking screw with threads on the outer surface of its head. The head of the screw may take several shapes from hemispherical to hexagonal recessed.

As used herein, the term "combination hole" or "combination aperture" is meant to refer a hole or aperture in a bone plate that is dimensioned and configured to have two portions or domains, each of which can accommodate a screw such that two screws can be positioned in the same combination hole.

As used herein, the term "bi-directional" or "bi-angular" in reference to a combination hole or aperture is meant to refer to a hole or aperture in a bone plate that is dimensioned and configured to accommodate two screws wherein, when the screws are positioned in the same hole, the screws are directed at angles to each other and to the bone plate, i.e., the directions of the two screws in the same combination hole are non-parallel.

The term "by-pass head" refers to a specialized screw in accordance with embodiments of the invention in which the head of the screw has a substantially circular or spherical segment, i.e., the head is cut by a chord or plane. The by-pass head screw may be locking or non-locking.

In view of the aforementioned disadvantages inherent in conventional bone fixation systems, a novel system and method for fixating bone fractures, especially long bone fractures, is provided. Given that many fractures have not only transverse fracture components but also oblique or, even rather frequently, long fracture lines along the bone, the inventor has been found that screw placement, in case of fracture fixation with a plate, directed away from a plane perpendicular to the bottom surface of the plate is advantageous. In one aspect, a bi-angular or bidirectional combination screw hole configuration in a bone plate is provided which is in the form of at least one, and suitably a plurality of, such combination holes or apertures, each hole of which has two domains for holding and positioning screws. One domain of the hole may be suitably used to mate a conventional bone screw, e.g., a non-locking screw, in one direction away from the perpendicular or even along the perpendicular to the bottom surface of the plate, while the other domain of the same combination hole is suitably used to mate a screw, e.g., a locking screw, in an entirely different non-parallel direction. In use, two screws may be suitably mated in each bi-angular hole wherein one screw is a conventional bone screw and the other is a by-pass head screw in accordance with embodiments of the invention. The direction of the screw placement per hole depends on the optimal configuration for individual fracture fixation and is not limited as in the existing prior art devices. It is also understood that the combination hole may accommodate two by-pass head screws as well.

Reference is now made to FIGS. 1-8 in which a bone fixation system, generally designated by reference numeral 10, in accordance with one embodiment of the invention is shown. System 10 includes a bone plate 20 and a screw system 21 for stabilizing bone segments. In one embodiment, bone plate 20 is defined by a first surface 22 and a second bone-contacting surface 24 that is opposed to the first surface 22. Bone plate 20 is suitably elongate, with a length 23 and a longitudinal axis 25. Bone plate 20 can optionally be curved along its length, enabling bone plate 20 to be anatomically contoured, i.e., to contour a bone surface.

In an illustrated embodiment, bone plate 20 includes a plurality of combination screw apertures or holes 26 which extend through the first and second surfaces 22, 24 of bone plate 20. Each of the combination apertures or holes 26 has a predefined shape and size. Each of the apertures or holes 26 is suitably shaped as a bi-angular or an offset figure-eight, and is dimensioned and configured to receive a pair of screws 32 and 34 therethrough. Screws 32, 34 are used to anchor bone plate 20 to the particular bone segments that require fixation, i.e., are suitable for insertion into bone. Each hole 26 has two domains 28 and 30, respectively, which are substantially circular but overlapping, forming an offset figure-eight overall shape. Each domain is dimensioned and configured to receive one of the pair of screws therethrough. Domains 28 and 30 may or may not be provided with internal threads 41. Internal threads 41 may engage the threads of a threaded head bone screw.

Figure 4:
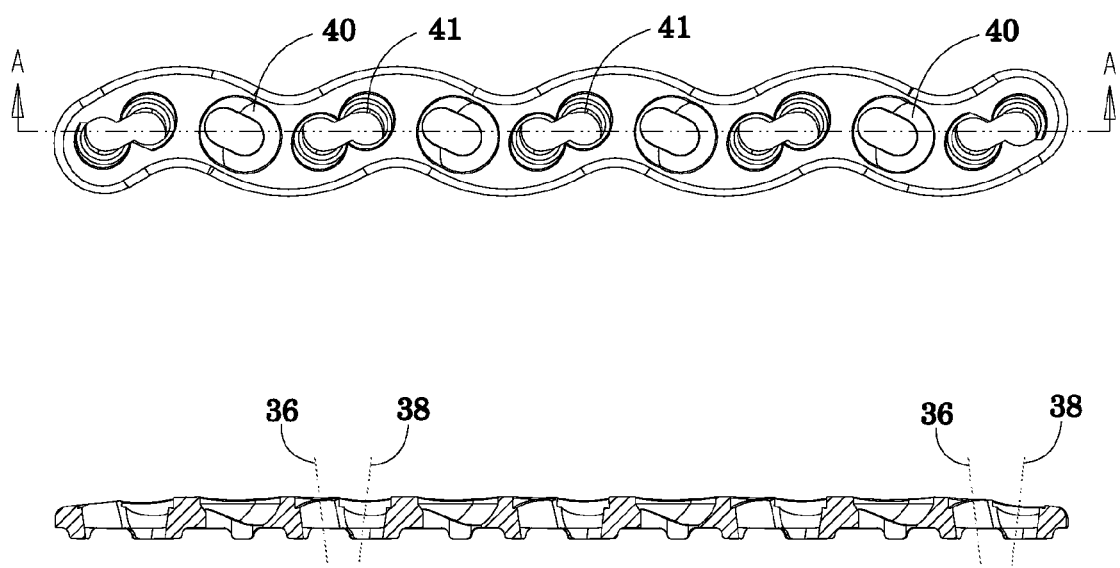
FIG. 4 is a top view of serpentine plate configuration and a cross-sectional view, along plane A-A', of the bi-directional divergent holes, illustrating the angled axes of the domains of each combination hole.
Figure 5:
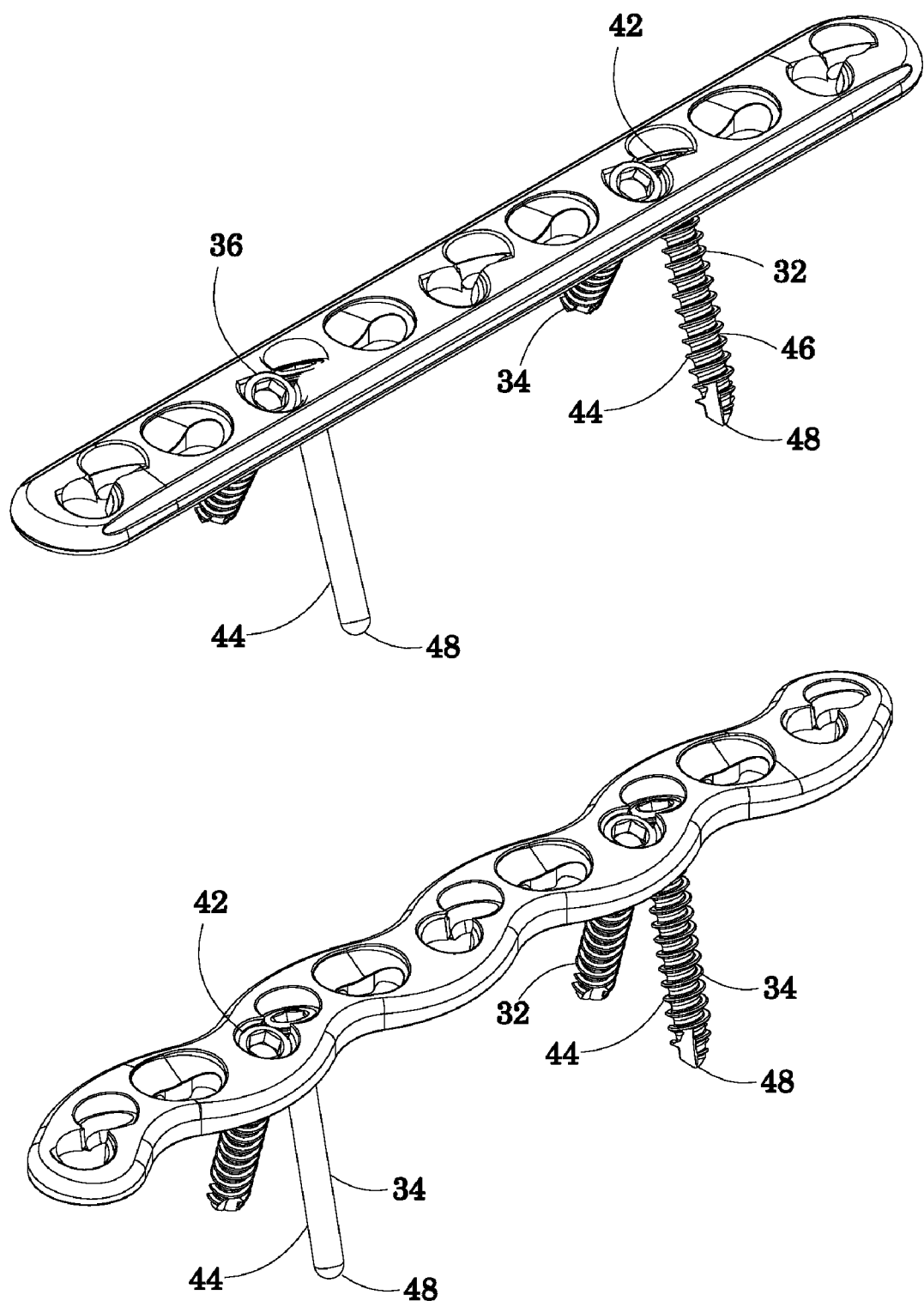
FIG. 5 is a perspective view of the directionality of individual screws when installed in bi-directional divergent holes.
Figure 6:
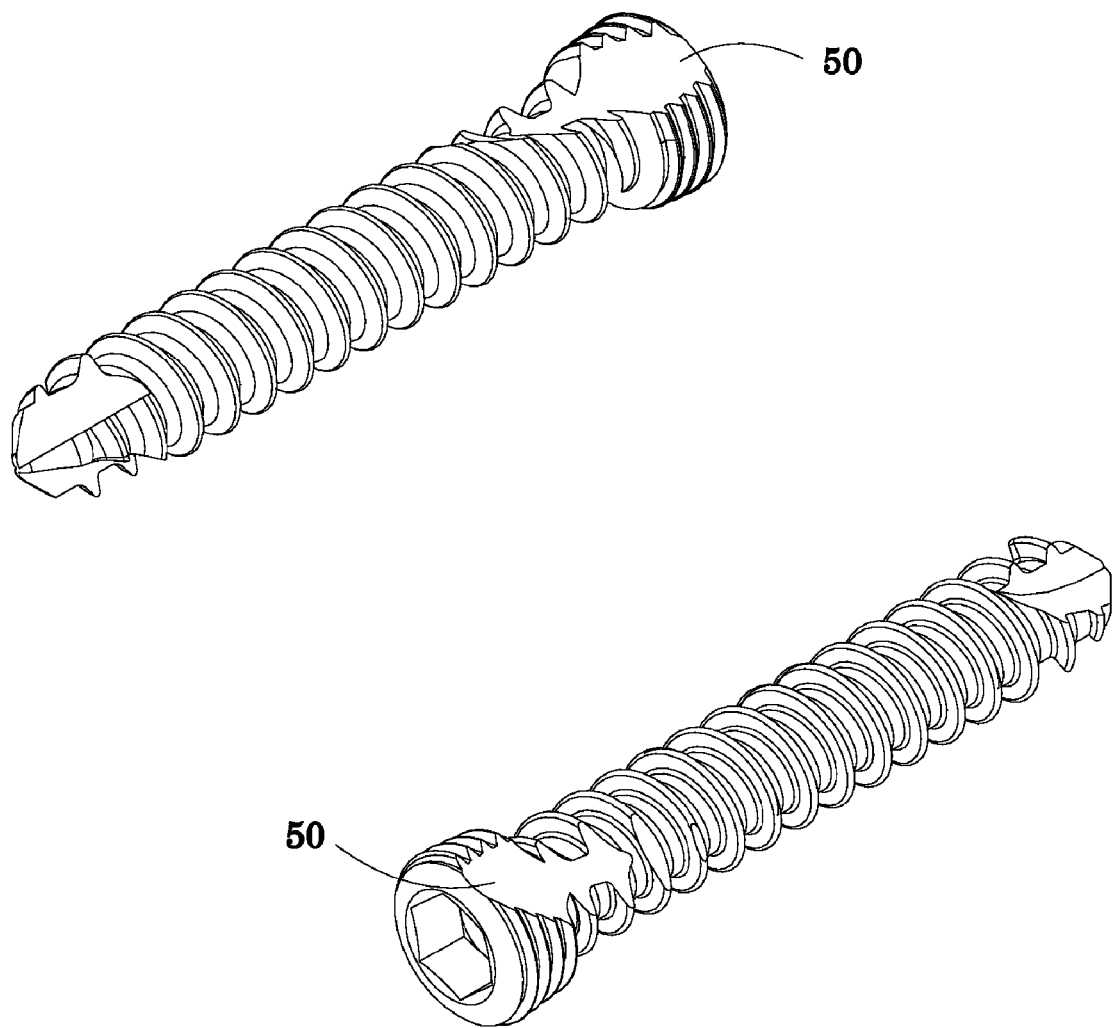
FIG. 6 is a perspective view of a by-pass locking screw in accordance with embodiments of the invention.
Figure 7:
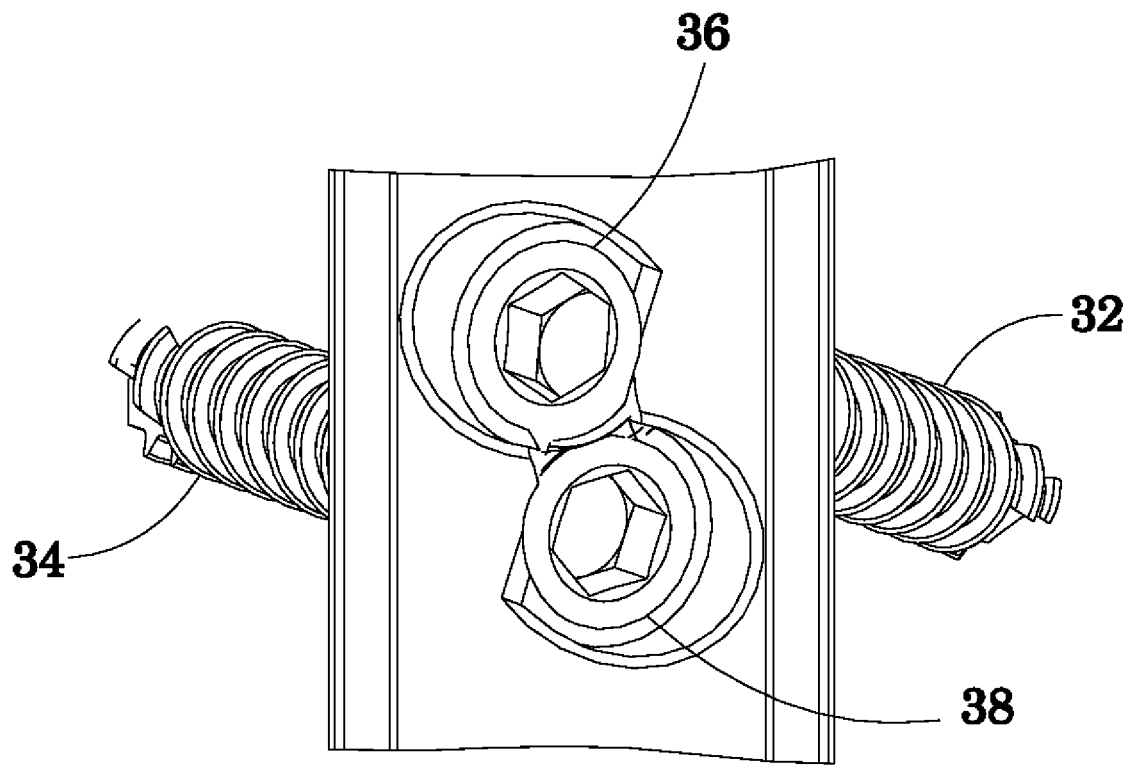
FIG. 7 is a top, cutaway view of a standard locking screw and a by-pass head screw, both positioned in the same bi-directional hole in accordance with embodiments of the invention.

Certain variations of the invention are set forth and illustrated in the figures. As shown in FIG. 4, one domain of a combination hole has a hole axis 36 and the other a hole axis is 38. The axes are angled with respect to each other, i.e., the axes are non-parallel. As shown in FIG. 7, screws 32, 34 have a head portion 36 and 38, respectively, at a proximal end 42. Each screw 32, 34 has an elongate body or shaft 44 that may include a threaded portion 46, as shown in FIG. 5, and/or a threaded head portion 45. Such external threads 45 disposed along the screw head can mately engage internal threads 41 of the domains of the bi-directional hole 26. It is understood that non-threaded screws or pegs as well as conventional threaded head screws can also be accommodated in bidirectional holes 26 as shown in FIG. 5.

Figure 2:
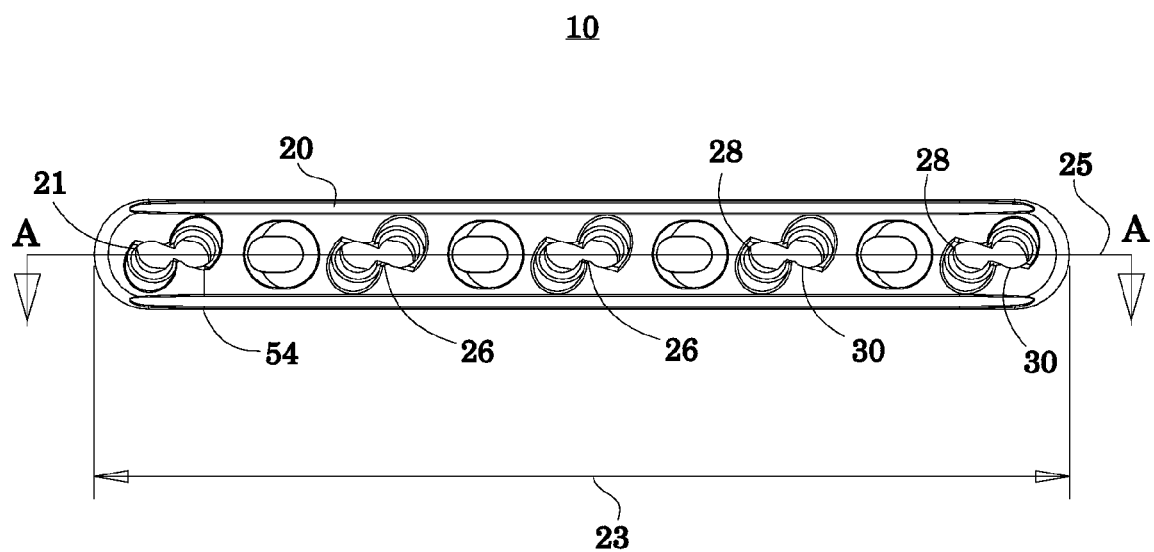
FIG. 2 is a top plan view of a linear plate configuration of a bone plate with a plurality of bi-directional screw holes, all in accordance with embodiments of the invention.
Figure 3:
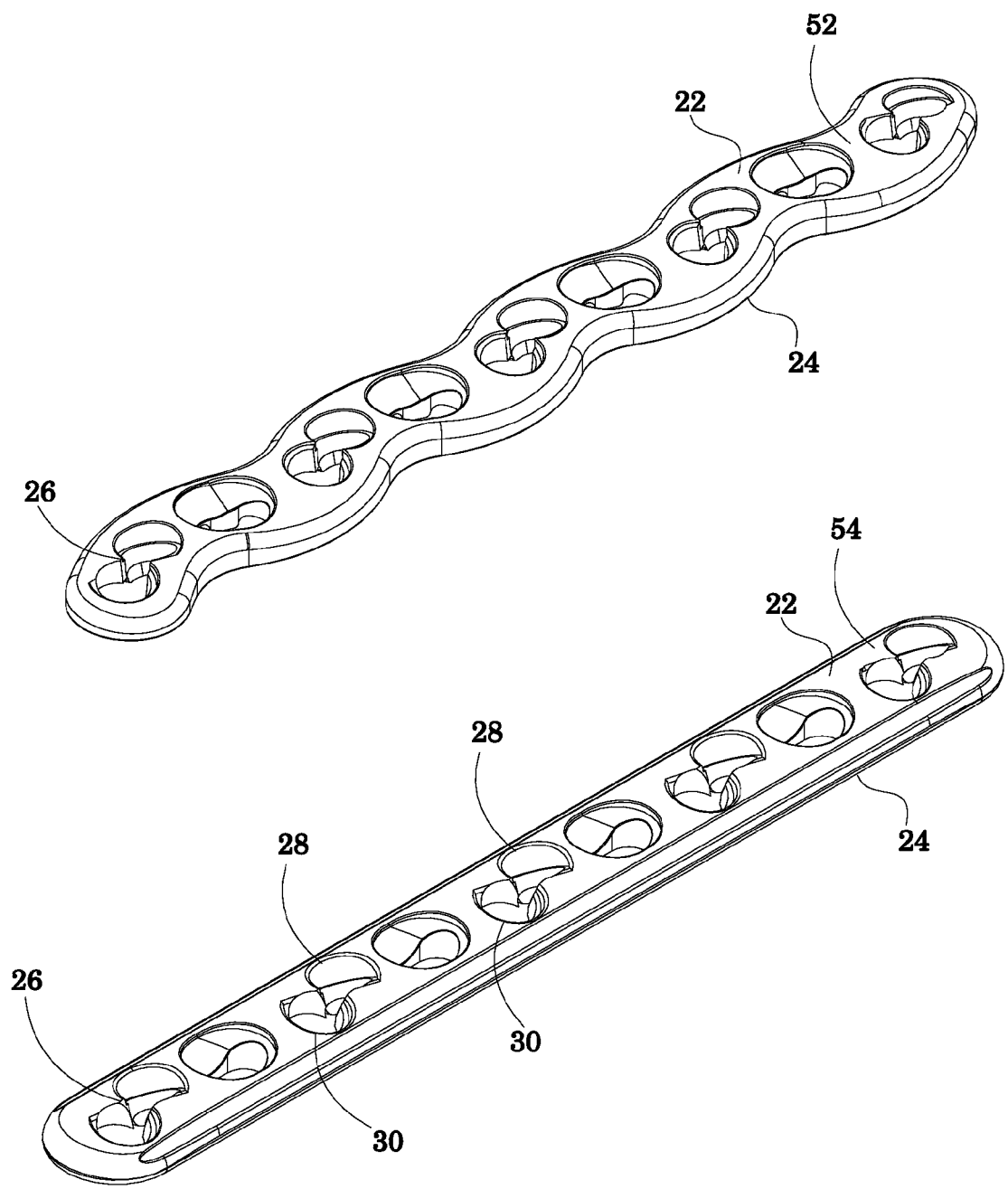
FIG. 3 depicts perspective views of the serpentine and linear bone plate configurations, illustrating both combination bi-directional holes and conventional holes.
Figure 8:
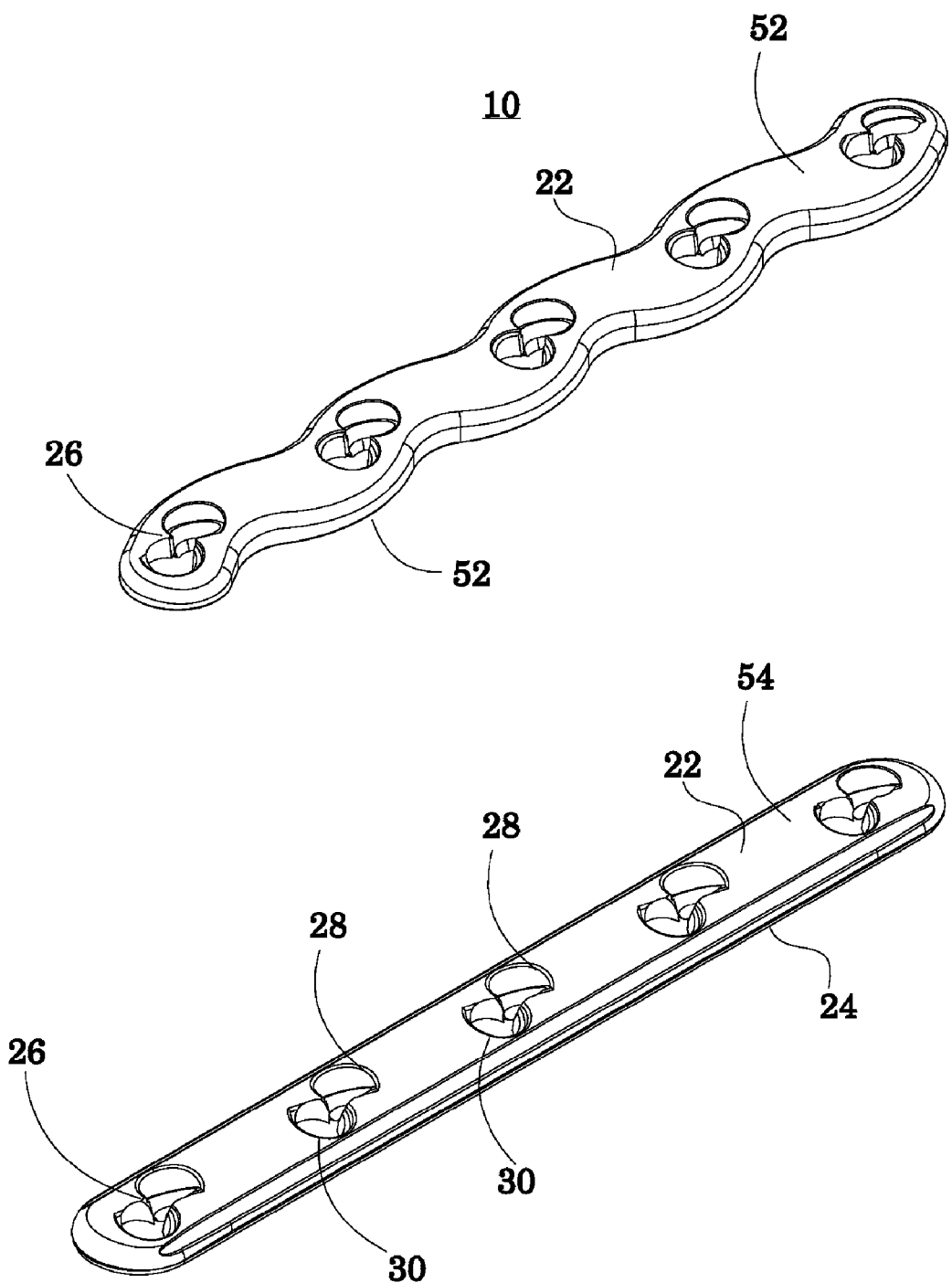
FIG. 8 depicts perspective views of the serpentine and linear bone plate configurations, having only combination bi-directional holes.

Bone plate 20 may have many shapes. In one variation, as shown in FIG. 1, bone plate 20 may have a suitably serpentine shape 52 with, e.g., an arched cross section contouring the bone surface. As described, the serpentine shape coupled with the angled combination holes permit a materials-conserving plate configuration. However, the plate can be configured in many different shapes and sizes to accommodate any situation. For example, FIG. 2 illustrates another variation of the invention as a linear plate configuration 54, and FIGS. 3 and 8 show perspective views of both the serpentine plate 52 and linear plate 54. The embodiments of FIG. 3 illustrate bone plate 20 with both combination bi-directional holes and conventional holes. The embodiments of FIG. 8 illustrates bone plate 20 having only combination bi-directional holes.

As described herein, in one variation, the underside of the bone plate may be concave, thus allowing the plate to conform to the rounded surface of the tibia, femur, humerus, forearm bone, and other bones with which embodiments of the invention may be used. The concave configuration of the underside also allows a conventional bone screw to be inserted obliquely through the plate hole when a small bone fragment must be gripped and pulled against the plate:

To accommodate two screws in a single combination hole, a conventional head, (e.g., substantially circular or hemispherical), bone screw 32 may be placed in at least one of the domains 28, 30 of holes 26 and provide compression of the fractured bone fragments. In the other domain, screw 34 has a by-pass head 50. By-pass head 50 of screw 34 allows two screws to be accommodated in the same single combination hole.

For example, a by-pass head screw may be placed eccentrically with respect to the hole, as is necessary for attaining compression of a fracture. With the by-pass head screw in place in the first domain of hole 26, the second domain of hole 26 may then receive the conventional full-head screw 32, as such variation is shown in FIG. 7. As described hereinabove, the second domain of the hole provides an increased angulation of the bone screw with respect to the bone plate and the other screw. That two divergent screws are mated to the same bi-angular hole provides additional fixation to bone because screws, oriented divergently into the bone, offer significantly more resistance to pull out than any existing configuration. Torsional resistance is also theoretically greatly increased. FIGS. 4-7 further illustrate embodiments of the invention with respect to the bi-directional screw holes and specialized by-pass screw head.

As noted, one of the two screws mated into the bi-angular hole can be a conventional nonlocking screw which is capable of bringing the bone to the plate. The other screw can then be mated to the plate and bone in a locking fashion. In current prior art devices, a surgeon has to sacrifice several holes to bring the bone to the plate and then use the remaining holes in a "locking mode". In accordance with the invention, no hole is "wasted" and every hole could offer enhanced fixation beyond what an existing locking or non-locking screw can.

Similarly, a non-locking by-pass head screw can be made to lock to the plate with a conventional locking screw that is mated to the adjacent domain of the same bi-angular screw. The bi-angular screw hole mated with two divergent screws provides added fixation in fractures adjacent to the softer bone proximate to joints, specifically, periarticular fractures and those that require articular subchondral support such as in distal radius fractures, tibial pilon fractures, tibial plateau fractures, etc.

Bone plate 20 may be provided with any number of holes 26 as may be suitable for a specific surgical application. Holes 26 may be disposed along the length 23 of bone plate 20; variations are illustrated, as shown, e.g., in FIGS. 1 and 2. One of ordinary skill in the art will know and appreciate that bone plate 20 may be provided with other types and configurations of holes 40, e.g., non-combination screw holes, in addition to combination holes 26, as illustrated. For example, in addition to one or a plurality of bi-directional combination screws, bone plate 20 may be provided with substantially cylindrical holes, threaded holes, or any other type of hole known to one of ordinary skill in the art.

To facilitate insertion, the threaded screws can be self-tapping screws or pre-drilled with the aide of a drill guide. Additionally, the screws can be cannulated for insertion of a guide wire to guide screw placement. As noted, the screws may have a smooth shaft such as a peg. The hole domains may have a substantially conical shape with a doublelead thread. The length of the individual screw shaft and the shaft (threaded or smooth) configuration can be selected for the particular application. For example, the individual screw shaft can also be smooth with a rounded, diamond, or trocar shaped tip. The domains may also be threaded or smooth, depending on whether the domain is accommodating a threaded screw or a peg.

In practice, embodiments of the invention provide methods of fixating bone fractures. The method includes positioning a bone plate having, along its length, a plurality of bi-directional divergent holes therethrough to a fracture site, inserting bone screws through the bi-directional holes of the bone plate into a bone or bone fragments to fixate the fracture, the screws being oriented in the bone in non-parallel directions.

It should also be noted that during the surgical act of applying the plate to the fractured bone, critical vessels or nerves or muscle or other soft tissue may be in the way of the path of the intended drill hole. In accordance with embodiments of the invention, a surgeon is able to avoid undue retraction on the soft tissue or even minimize soft tissue dissection by choosing the more suitable direction afforded by the bi-directional hole design. Therefore, an additional benefit of the bi-directional design is its versatility, minimizing the requirement for soft tissue dissection and retraction.

In summary, the full mechanical advantage of the combination hole configuration in accordance with embodiments of the invention is realized when two screws are mated to the same bi-directional or bi-angular hole. The head of one screw to be mated to the plate suitably has a by-pass head to allow the placement in the same hole of a second screw with a conventional full-headed screw. Having two fixed-angle screws oriented in divergent directions into the substance of the bone enhances the pull out strength of the plate from the bone far beyond that of a single locking screw oriented perpendicular to the plate.

The foregoing description is considered as illustrative only of the principles manifest in embodiments of the invention. Further, since numerous modifications and changes may readily occur to those skilled in the art, it is not desired to limit the invention to the exact construction and operation shown and described, and accordingly, all suitable modifications and equivalents are considered to fall within the scope of the invention. Various features and advantages of the invention are set forth in the following claims.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A bone fixation system adapted to stabilize at least two bone portions of a fractured bone, the bone fixation system comprising:
   a plate having a mid-longitudinal axis, a first end, a second end, a length between said first and second ends, and a width less than and perpendicular to said length, said length being sufficient to overlap the at least two bone portions, said plate having an upper surface, a lower surface, and a thickness between said upper and lower surfaces, said lower surface being opposite said upper surface, the mid-longitudinal axis extending through said first and second ends and along said length of said plate;
   at least one bi-directional hole extending through said plate from said upper surface to said lower surface, said at least one bi-directional hole having a first bone fastener receiving portion, a second bone fastener receiving portion, and a connecting portion between said first and second bone fastener receiving portions, said first bone fastener receiving portion including a central longitudinal axis extending between said upper and lower surfaces, and said second bone fastener receiving portion including a central longitudinal axis extending between said upper and lower surfaces, the central longitudinal axes of said first and second bone fastener receiving portions diverging from one another below said lower surface of said plate, the central longitudinal axes of said first and second bone fastener receiving portions being transverse to a first plane extending along the mid-longitudinal axis of said plate and the first plane being perpendicular to said upper surface of said plate, and the central longitudinal axes of said first and second bone fastener receiving portions extending in second and third planes, respectively, said second and third planes being parallel to one another and crossing the mid-longitudinal axis at different points along said length of said plate, said first and second bone fastener receiving portions being threaded; and
   at least two bone fasteners, each of said at least two bone fasteners including a head portion adapted to engage said plate and a shaft portion adapted to engage the fractured bone, a first bone fastener of said at least two bone fasteners being received and seated in said first bone fastener receiving portion and a second bone fastener of said at least two bone fasteners being received and seated in said second bone fastener receiving portion, said head portions having threads formed thereon, said threads of said head portions of said first and second bone fasteners being adapted to engage said threads of said first and second bone fastener receiving portions, respectively, one of said first and second bone fasteners including a cut-out portion formed on said head portion thereof, said cut-out portion interrupting said threads formed on said head portion of said one of said first and second bone fasteners, said first and second bone fasteners, when received in said first and second bone fastener receiving portions, respectively, being oriented at angles aligned with the central longitudinal axes of said respective first and second bone fastener receiving portions, and diverging from one another below said lower surface of said plate, wherein, when said one of said first and second bone fasteners is seated in one of said first and second bone fastener receiving portions, and said cut-out portion is oriented toward said connecting portion between said first and second bone fastener receiving portions, said cut-out portion allowing passage of said head portion of the other of said first and second bone fasteners into the other of said first and second bone fastener receiving portions, said head of said one of said first and second bone fasteners including said cut-out portion having a cross sectional configuration through said head such that if said cut-out portion is oriented away from said connecting portion between said first and second bone fastener receiving portions when seated in said one of said first and second bone fastener receiving portions, said cross sectional configuration of said head prevents passage of said head portion of the other of said first and second bone fasteners into the other of said first and second bone fastener receiving portions, said head portion of the other of said first and second bone fasteners directly abutting said cut-out portion of said one of said first and second bone fasteners.

2. The bone fixation system of claim 1, wherein said head portion of the other of said first and second bone fasteners directly abutting said cut-out portion of said one of said first and second bone fasteners blocks rotation of said one of said first and second bone fasteners including said cut-out portion.

3. The bone fixation system of claim 1, wherein said shaft portions of said first and second bone fasteners are at least partially threaded, said first and second bone fasteners being screws.

4. The bone fixation system of claim 3, further comprising a tip included on each of said first and second bone screws, wherein said threads provided on each of said shaft portions are interrupted adjacent said tips.

5. The bone fixation system of claim 3, further comprising a tip included on each of said first and second bone screws, said shafts of said first and second bone screws tapering toward said tips.

6. The bone fixation system of claim 1, wherein at least a portion of said lower surface of said plate is concave.

7. The bone fixation system of claim 1, wherein said first bone fastener receiving portion includes an arcuate portion at said upper surface extending around at least 180 degrees on a first side of the mid-longitudinal axis of said plate, and said second bone fastener receiving portion includes an arcuate portion at said upper surface extending around at least 180 degrees on a second side of the mid-longitudinal axis of said plate.

8. The bone fixation system of claim 7, wherein said first bone fastener receiving portion includes a straight portion at said upper surface on the second side of the mid-longitudinal axis of said plate, and said second bone fastener receiving portion includes a straight portion at said upper surface on the first side of the mid-longitudinal axis of said plate, said straight portions of said first and second bone fastener receiving portions are substantially parallel to one another.

9. The bone fixation system of claim 1, wherein said first and second bone fastener receiving portions communicate with one another via said connecting portion.

10. The bone fixation system of claim 1, wherein the central longitudinal axes of said first and second bone fastener receiving portions is offset from one another along said length of said plate, and the central longitudinal axes of said first and second bone fastener receiving portions extending through said upper surface of said plate on opposite sides of the mid-longitudinal axis of said plate.

11. The bone fixation system of claim 1, wherein said shaft portions of said first and second bone fasteners are fully threaded.

12. The bone fixation system of claim 1, wherein said shaft portions of said first and second bone fasteners are unthreaded.

13. The bone fixation system of claim 1, wherein said shaft portions of said first and second bone fasteners comprise cannulated shafts adapted for insertion over guide wires.

14. A bone fixation system adapted to stabilize at least two bone portions of a fractured bone, the bone fixation system comprising:
a plate having a mid-longitudinal axis, said plate having a first end, a second end, a length between said first and second ends, and a width less than and perpendicular to said length, said length being sufficient to overlap the at least two bone portions, said plate having an upper surface, a lower surface, and a thickness between said upper and lower surfaces, said lower surface being opposite said upper surface, the mid-longitudinal axis extending through said first and second ends and along said length of said plate;
at least one bi-directional hole extending through said plate from said upper surface to said lower surface, said at least one bi-directional hole having a first bone fastener receiving portion, a second bone fastener receiving portion, and a connecting portion between said first and second bone fastener receiving portions, said first bone fastener receiving portion including a central longitudinal axis extending between said upper and lower surfaces, and said second bone fastener receiving portion including a central longitudinal axis extending between said upper and lower surfaces, the central longitudinal axes of said first and second bone fastener receiving portions diverging from one another below said lower surface of said plate, the central longitudinal axes of said first and second bone fastener receiving portions being offset from one another along said length of said plate, and the central longitudinal axes of said first and second bone fastener receiving portions extending through said upper surface of said plate on opposite sides of the mid-longitudinal axis of said plate, said first and second bone fastener receiving portions being threaded; and
at least two bone fasteners, each of said at least two bone fasteners including a head portion adapted to engage said plate and a shaft portion adapted to engage the fractured bone, a first bone fastener of said at least two bone fasteners being received and seated in said first bone fastener receiving portion and a second bone fastener of said at least two bone fasteners being received and seated in said second bone fastener receiving portion, said head portions having threads formed thereon, said threads of said head portions of said first and second bone fasteners being adapted to engage said threads of said first and second bone fastener receiving portions, respectively, one of said first and second bone fasteners includes a cut-out portion formed on said head portion thereof, said cut-out portion interrupting said threads formed on said head portion of said one of said first and second bone fasteners, said first and second bone fasteners, when received in said first and second bone fastener receiving portions, respectively, being oriented at angles aligned with the central longitudinal axes of said respective first and second bone fastener receiving portions, and diverging from one another below said lower surface of said plate, wherein, when said one of said first and second bone fasteners is seated in one of said first and second bone fastener receiving portions, and said cut-out portion is oriented toward said connecting portion between said first and second bone fastener receiving portions, said cut-out portion allowing passage of said head portion of the other of said first and second bone fasteners into the other of said first and second bone fastener receiving portions, said head of said one of said first and second bone fasteners including said cut-out portion having a cross sectional configuration through said head such that if said cut-out portion is oriented away from said connecting portion between said first and second bone fastener receiving portions when seated in said one of said first and second bone fastener receiving portions, said cross sectional configuration of said head prevents passage of said head portion of the other of said first and second bone fasteners into the other of said first and second bone fastener receiving portions, said head portion of the other of said first and second bone fasteners directly abutting said cut-out portion of said one of said first and second bone fasteners.

15. The bone fixation system according to claim 14, wherein said head portion of the other of said first and second bone fasteners directly abutting said cut-out portion of said one of said first and second bone fasteners blocks rotation of said one of said first and second bone fasteners including said cut-out portion.

16. The bone fixation system according to claim 14, wherein at least a portion of said lower surface of said plate is concave.

17. The bone fixation system according to claim 14, wherein the mid-longitudinal axis of said plate delineates a first side and a second side, said first bone fastener receiving portion including a straight portion at said upper surface on said first side of the mid-longitudinal axis of said plate, and said second bone fastener receiving portion including a straight portion at said upper surface on said second side of the mid-longitudinal axis of said plate, said straight portions of said first and second bone fastener receiving portions being substantially parallel to one another.

18. The bone fixation system according to claim 14, wherein said first and second bone fastener receiving portions communicate with one another via said connecting portion.

19. The bone fixation system of claim 14, wherein said shaft portions of said first and second bone fasteners are at least partially threaded.

20. The bone fixation system of claim 14, wherein said shaft portions of said first and second bone fasteners are fully threaded.

21. The bone fixation system of claim 14, wherein said shaft portions of said first and second bone fasteners are unthreaded.

22. The bone fixation system of claim 14, wherein said shaft portions of said first and second bone fasteners comprise cannulated shafts adapted for insertion over guide wires.

23. A bone fixation system adapted to stabilize at least two bone portions of a fractured bone, the bone fixation system comprising:
 a plate having a mid-longitudinal axis delineating a first side and a second side of said plate, said plate having a first end, a second end, a length between said first and second ends, and a width less than and perpendicular to said length, said length being sufficient to overlap the at least two bone portions, said plate having an upper surface, a lower surface, and a thickness between said upper and lower surfaces, said lower surface being opposite said upper surface, the mid-longitudinal axis extending through said first and second ends and along said length of said plate;
 at least one bi-directional hole extending through said plate from said upper surface to said lower surface, said at least one bi-directional hole having a first bone fastener receiving portion being threaded, a second bone fastener receiving portion being threaded, and a connecting portion between said first and second bone fastener receiving portions, said first bone fastener receiving portion including a first central longitudinal axis extending between said upper and lower surfaces and a first radius measured from the first central longitudinal axis to a first side wall proximate said upper surface, and said second bone fastener receiving portion including a second central longitudinal axis extending between said upper and lower surfaces and a second radius measured from the second central longitudinal axis to a second side wall proximate said upper surface, said first bone fastener receiving portion including a first arcuate portion having a first arc of radius at said upper surface extending continuously around at least 180 degrees on said first side of the mid-longitudinal axis of said plate, said first arcuate portion of said first bone fastener receiving portion beginning on said second side of the mid-longitudinal axis, and said second bone fastener receiving portion including a second arcuate portion having a second arc of radius at said upper surface extending continuously around at least 180 degrees on said second side of the mid-longitudinal axis of said plate, said arcuate portion of said second bone fastener receiving portion beginning on said first side of the mid-longitudinal axis, the first arc of radius of said first arcuate portion intersecting the second arc of radius of said second arcuate portion, said first central longitudinal axis proximate said upper surface being spaced from said second central longitudinal axis proximate said upper surface a distance less than a combination of the first arc of radius and of the second arc of radius; and
 at least two bone fasteners, each of said at least two bone fasteners including a head portion adapted to engage said plate and a shaft portion adapted to engage the fractured bone, a first bone fastener of said at least two bone fasteners being received and seated in said first bone fastener receiving portion and a second bone fastener of said at least two bone fasteners being received and seated in said second bone fastener receiving portion, said head portions having threads formed thereon, said threads of said head portions of said first and second bone fasteners being adapted to engage said threads of said first and second bone fastener receiving portions, respectively, a majority portion of said head of said first bone fastener being provided on said first side of the mid-longitudinal axis of said plate and another portion of said head of said first bone fastener being provided on said second side of said plate and said shaft portion of said first bone fastener being angled toward said second side of the mid-longitudinal axis of said plate, a majority portion of said second bone fastener being provided on said second side of said plate and another portion of said head of said second bone fastener being provided on said first side of said plate and said shaft portion of said second bone fastener being angled toward said first side of said plate, one of said first and second bone fasteners includes a cut-out portion formed on said head portion thereof, said cut-out portion interrupting said threads formed on said head portion of said one of said first and second bone fasteners, said first and second bone-fasteners, when received in said first and second bone fastener receiving portions, respectively, being oriented at angles aligned with the central longitudinal axis of said respective first and second bone fastener receiving portions, and diverging from one another below said lower surface of said plate, wherein, when said one of said first and second bone fasteners is seated in one of said first and second bone fastener receiving portions, and said cut-out portion is oriented toward said connecting portion between said first and second bone fastener receiving portions, said cut-out portion allowing passage of said head portion of the other of said first and second bone fasteners into the other of said first and second bone fastener receiving portions, said head portion of the other of said first and second bone fasteners directly abutting said cut-out portion of said one of said first and second bone fasteners so that said head portion of the other of said first and second bone fasteners blocks rotation of said one of said first and second bone fasteners including said cut-out portion.

24. The bone fixation system of claim 23, wherein said shaft portions of said first and second bone fasteners being at least partially threaded.

25. The bone fixation system of claim 23, wherein said shaft portions of said first and second bone fasteners are fully threaded.

26. The bone fixation system of claim 23, wherein said shaft portions of said first and second bone fasteners are unthreaded.

27. The bone fixation system of claim 23, wherein said shaft portions of said first and second bone fasteners comprise cannulated shafts adapted for insertion over guide wires.

28. A bone fixation system adapted to stabilize at least two bone portions of a fractured bone, the bone fixation system comprising:
 a plate having a mid-longitudinal axis delineating a first side and a second side of said plate, said plate having a first end, a second end, a length between said first and second ends, and a width less than and perpendicular to said length, said length being sufficient to overlap the at least two bone portions, said plate having an upper surface, a lower surface, and a thickness between said upper and lower surfaces, said lower surface being opposite said upper surface, the mid-longitudinal axis extending through said first and second ends and along said length of said plate;

at least one bi-directional hole extending through said plate from said upper surface to said lower surface, said at least one bi-directional hole having a first bone fastener receiving portion being threaded, a second bone fastener receiving portion being threaded, and a connecting portion between said first and second bone fastener receiving portions, said first bone fastener receiving portion including a first central longitudinal axis extending between said upper and lower surfaces and a first radius measured from the first central longitudinal axis to a first side wall proximate said upper surface, and said second bone fastener receiving portion including a second central longitudinal axis extending between said upper and lower surfaces and a second radius measured from the second central longitudinal axis to a second side wall proximate said upper surface, a majority portion of said first bone fastener receiving portion being provided on said first side of said plate and another portion of said first bone fastener receiving portion being provided on said second side of said plate, a majority portion of said second bone fastener receiving portion being provided on said second side of said plate and another portion of said second bone fastener receiving portion being provided on said first side of said plate, said first and second bone fastener receiving portions communicating via said connecting portion, said connecting portion extending across the mid-longitudinal axis of said plate, and said connecting portion adapted to receive portions of at least two bone fasteners; and at least two bone fasteners, each of said at least two bone fasteners including a head portion adapted to engage said plate and a shaft portion adapted to engage the fractured bone, a first bone fastener of said at least two bone fastener being received and seated in said first bone fastener receiving portion and a second bone fastener of said at least two bone fasteners being received and seated in said second bone fastener receiving portion, said head portions having threads formed thereon, said threads of said head portions of said first and second bone fasteners being adapted to engage said threads of said first and second bone fastener receiving portions, respectively, a majority portion of said head of said first bone fastener being provided on said first side of the mid-longitudinal axis of said plate and another portion of said head of said first bone fastener being provided on said second side of said plate and said shaft portion of said first bone fastener being angled toward said second side of the mid-longitudinal axis of said plate, a majority portion of said second bone fastener being provided on said second side of said plate and another portion of said head of said second bone fastener being provided on said first side of said plate and said shaft portion of said second bone fastener being angled toward said first side of said plate, one of said first and second bone fasteners includes a cut-out portion formed on said head portion thereof, said cut-out portion interrupting said threads formed on said head portion of said one of said first and second bone fasteners, said first and second bone-fasteners, when received in said first and second bone fastener receiving portions, respectively, being oriented at angles aligned with the central longitudinal axes of said respective first and second bone fastener receiving portions, and diverging from one another below said lower surface of said plate, wherein, when said one of said first and second bone fasteners is seated in one of said first and second bone fastener receiving portions, and said cut-out portion is oriented toward said connecting portion between said first and second bone fastener receiving portions, said cut-out portion allowing passage of said head portion of the other of said first and second bone fasteners into the other of said first and second bone fastener receiving portions, said head portion of the other of said first and second bone fasteners directly abutting said cut-out portion of said one of said first and second bone fasteners so that said head portion of the other of said first and second bone fasteners blocks rotation of said one of said first and second bone fasteners including said cut-out portion.

29. The bone fixation system of claim 28, wherein said shaft portions of said first and second bone fasteners are at least partially threaded.

* * * * *

UNITED STATES PATENT AND TRADEMARK OFFICE
CERTIFICATE OF CORRECTION

PATENT NO. : 8,764,808 B2  
APPLICATION NO. : 13/439725  
DATED : July 1, 2014  
INVENTOR(S) : Eduardo Gonzalez-Hernandez Page 1 of 1

It is certified that error appears in the above-identified patent and that said Letters Patent is hereby corrected as shown below:

Title Page 1, Item (56), References Cited, Other Publications:
Column 2, line 21, change "Velar" to -- Volar --;

Title Page 3, Item (56), References Cited, Other Publications:
Column 2, line 23, change "[B]" to -- [Br] --;
Column 2, line 24, change "e.t al.," to -- et al., --;
Column 2, line 29, change "http://wwvv.jpgmonline.com/articie.asp?issn,=0022-"
        to -- http://www.jpgmonline.com/article.asp?issn=0022 --;
Column 2, line 38, change "55(6).1139-44" to -- 55(6):1139-44 --;
Column 2, line 40, change "2003:" to -- 2003; --.

Signed and Sealed this  
Tenth Day of February, 2015

Michelle K. Lee  
*Deputy Director of the United States Patent and Trademark Office*